United States Patent [19]

Heubeck

[11] Patent Number: 4,847,881

[45] Date of Patent: Jul. 11, 1989

[54] DENTAL X-RAY DIAGNOSTICS INSTALLATION FOR PRODUCING PANORAMA TOMOGRAMS OF THE JAW OF A PATIENT

[75] Inventor: Erich Heubeck, Bensheim, Fed. Rep. of Germany

[73] Assignee: Siemens Aktiengesellschaft, Berlin and Munich, Fed. Rep. of Germany

[21] Appl. No.: 942,720

[22] Filed: Dec. 17, 1986

[30] Foreign Application Priority Data

Dec. 20, 1985 [DE] Fed. Rep. of Germany ....... 3545509

[51] Int. Cl.⁴ ............................................. G03B 41/16
[52] U.S. Cl. ........................................ 378/38; 378/40
[58] Field of Search ..................... 378/38, 39, 40, 116, 378/115, 21, 27

[56] References Cited

U.S. PATENT DOCUMENTS

| | | |
|---|---|---|
| 3,908,126 | 9/1975 | Hudson et al. . |
| 3,952,200 | 4/1976 | Winkler ................... 378/21 |
| 4,039,837 | 8/1977 | Ohta et al. . |
| 4,194,121 | 3/1980 | Cushman ................ 378/39 |
| 4,242,585 | 12/1980 | Yamano ................ 378/116 |
| 4,418,419 | 11/1983 | Schreiber .............. 378/40 |
| 4,442,534 | 4/1984 | Haendle et al. ....... 378/21 |

FOREIGN PATENT DOCUMENTS 1244555 7/1967 Fed. Rep. of Germany .

OTHER PUBLICATIONS

"Putting the Optiplanimat X-ray Planigraphic Unit to the Test in the Daily Routine," Ulbricht, Siemens Electromedica, vol. 4, 1978, pp. 133–135.
Siemens brochure for Orthopantomograph ®10.

Primary Examiner—Craig E. Church

[57] ABSTRACT

A dental x-ray diagnostics installation for generating panorama tomograms of a patient has a rotary unit on which a radiation source and a carrier for a film cassette are mounted. The rotary unit is mounted so as to be rotatable around a vertical axis and can also be swivelled at right angles relative to the axis of symmetry of the patient while simultaneously undergoing rotational motion. The mount for the film cassette can be adjusted relative to the radiation source independently of adjustment of the rotary unit. A control unit operates the rotary unit so that, proceeding from an initial position, the rotary unit is repeatedly rotated by a selected angle corresponding to a desired area to be examined, and further controls the drive for the film cassette at a speed corresponding to a selected tomogram position upon each repeated transillumination of the subject.

17 Claims, 3 Drawing Sheets

DENTAL X-RAY DIAGNOSTICS INSTALLATION FOR PRODUCING PANORAMA TOMOGRAMS OF THE JAW OF A PATIENT

BACKGROUND OF THE INVENTION

1. Field of the Invention

The present invention relates to an x-ray apparatus for dental use for generating panorama tomograms of the jaw of a patient.

2. Related Applications

The subject matter disclosed herein is related to the subject matter disclosed in the following applications: Ser. No. 942,812 filed Dec. 17, 1986 (Erich Heubeck, Werner Guenther, Manfred Muether and Leonard Werner); Ser. No. 942,800 filed Dec. 17, 1986 (Michael Doebert); and Ser. No. 942,747 filed Dec. 17, 1986 (Erich Heubeck, Manfred Muether and Dieter Molitor).

3. Description of the Prior Art

X-ray devices, and supporting structure therefore, are known in the art for generating a panorama tomogram of the jaw of a patient, wherein the x-ray source and a carrier for a film cassette are disposed at opposite sides of a rotary unit, with the holder for the film cassette being adjustably disposed such that x-rays from the radiation source are incident on the film substantially perpendicularly thereto. Such installations include an adjustment mechanism for adjusting the position of the film carrier in a curve corresponding to the mandibular arch so that the teeth can be successively imaged on the film in combination with the jaw.

In conventional x-ray diagnostics installations of this type as described, for example, in Brochure M-D 80/1361 for the ORTHOPANTOMOGRAPH 10, such exposures are possible only in a tomogram position permanently fixed for the apparatus. In order to make a larger diagnosis region available for standard or routine examinations, the exposure sequence is selected to obtain the greatest possible slice thickness. Because of such a large slice thickness, however, superimposed images can occur in which case important diagnostic details of the examination subject may be disposed behind one another. In some circumstances, this may lead to an incorrect diagnosis, or prevent a diagnosis being made at all.

From general x-ray technology, it is known to generate a plurality of parallel body slices simultaneously in x-ray images. This is known as the so-called "simultaneous slice method" and is described, for example, in German AS No. 12 44 555. Devices of this type cannot be used for panorama exposures, however, because a plurality of films having intensifier foils (film foil sets) must be arranged in a stack in a cassette, and the individual foil sets must be displaced parallel to each other during the exposure. This cannot be accomplished using rotational movement as is necessary to obtain a panorama tomogram.

SUMMARY OF THE INVENTION

It is an object of the present invention to provide a dental x-ray diagnostic installation wherein x-ray exposures on a film in a plurality of tomogram positions can be obtained.

In accordance with the principles of the present invention, the above object is achieved in a dental x-ray installation having a rotary unit having a ring on which a radiation source and a holder for a film cassette are disposed opposite each other so that x-rays from the radiation source are incident substantially perpendicularly on the film cassette. An adjustment mechanism permits the carrier ring to be adjusted in an orbital curve corresponding to the mandibular arch, such that the teeth are successively imaged on the film in combination with the jaw. The adjustment mechanism includes a first adjustment means by which the carrier ring can be rotated around a vertical axel bearing, and a second adjustment means which permits the carrier ring to be swivelled at right angles relative to the axis of symmetry of the examination subject while simultaneously executing the rotational motion around the vertical axle. The swivel radius and the amount of swivel motion are selected such that, upon rotation of the carrier ring, a perpendicular transillumination direction through the subject is always maintained at a substantially constant spacing between the subject and the film.

The film cassette is adjustable relative to the radiation source independently of the adjustment means for the rotary ring.

A control unit controls motion of the carrier ring so that, proceeding from an initial position, the ring is repeatedly advanced by a selected angle corresponding to a portion of the subject to be examined. The radiation source is energized at the beginning of each adjustment and is de-energized after the adjustment angle has been traversed. The control unit also controls the drive for the film cassette for advancing the film therein at each repetition of transillumination of the subject at a speed corresponding to a selected tomogram position. The control unit also advances the film in the film cassette by an amount corresponding to an imaging excerpt relative to the radiation source after each repetition of the transillumination of the subject.

DESCRIPTION OF THE PREFERRED EMBODIMENTS

Figure 1:
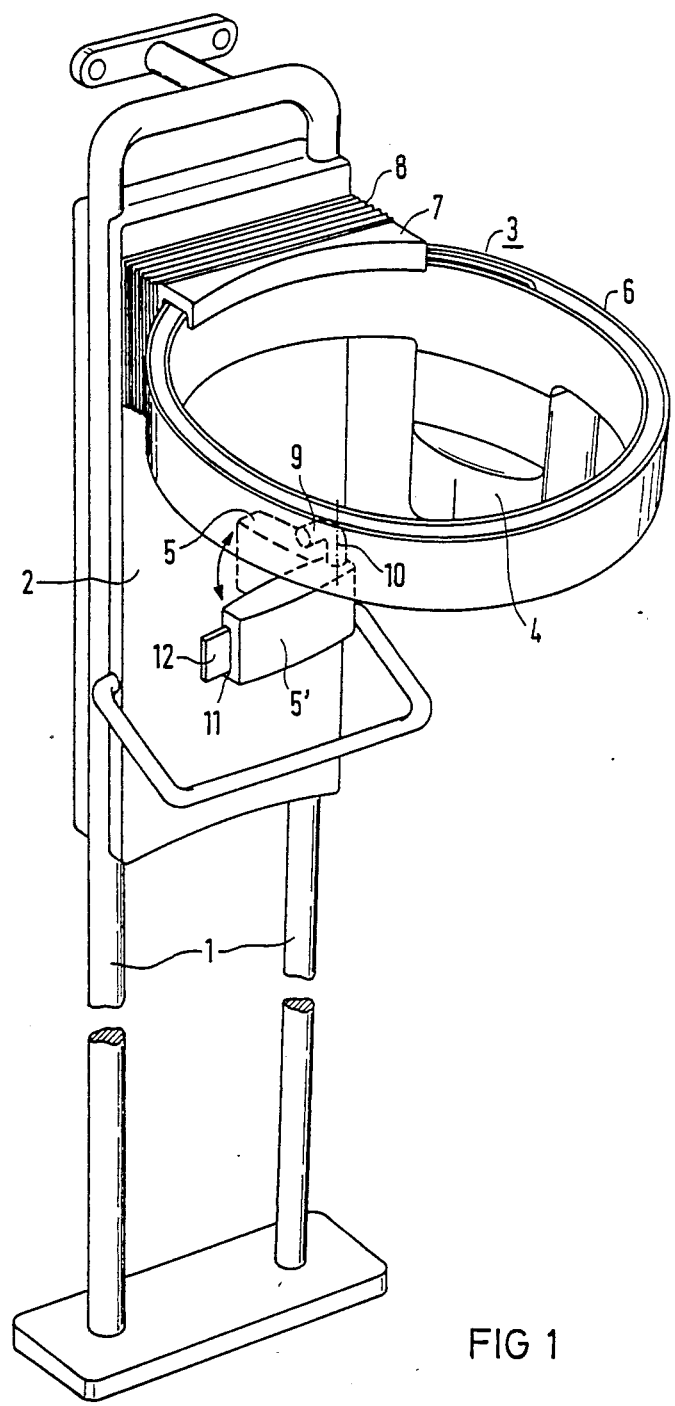
FIG. 1 is a perspective view of a dental x-ray diagnostics installation constructed in accordance with the principles of the present invention.

An x-ray diagnostic installation constructed in accordance with the principles of the present invention is shown in FIG. 1. The installation has a supporting structure including two standards 1 which receive a sliding truck 2 therebetween so that the height of the truck 2 can be adjusted. The truck 2 carries a rotary unit generally referenced at 3 which includes a ring 6 on which an x-ray source 4 and a film cassette holder 5 are mounted opposite each other. The radiation source 4, and thus its beam exit opening, are rotationally fixed with respect to the ring 6, whereas the film cassette holder 5 is independently pivotable in the direction of the arrow on a vertical axis 10 having an angled arm 9. The film cassette holder 5 can thus be brought from a use position (shown in broken lines) to a non-use position 5' (shown with solid lines). This permits the technician to more easily position the head of the patient and also enables generation of remote exposures (so-called Ceph exposures) for which the x-ray source had to be rotated in conventional installations.

The film cassette holder 5 has slot-like entry and exit openings 11 at both end faces through which a film cassette 12 can be introduced or withdrawn. The film cassette is flexible and is provided with an intensifier foil as is known for intraoral exposures. Transport of the film cassette 12 through the cassette holder 5 is accomplished by an electromotive drive M4 (shown in FIG. 2). The ring 6 is rotatably held in a bearing 7 and is pivotable relative to the truck 2. The adjustment mechanism, shown in greater detail in FIG. 2 between the truck 2 and the ring 6, is covered by an accordian bellows 8.

Figure 2:
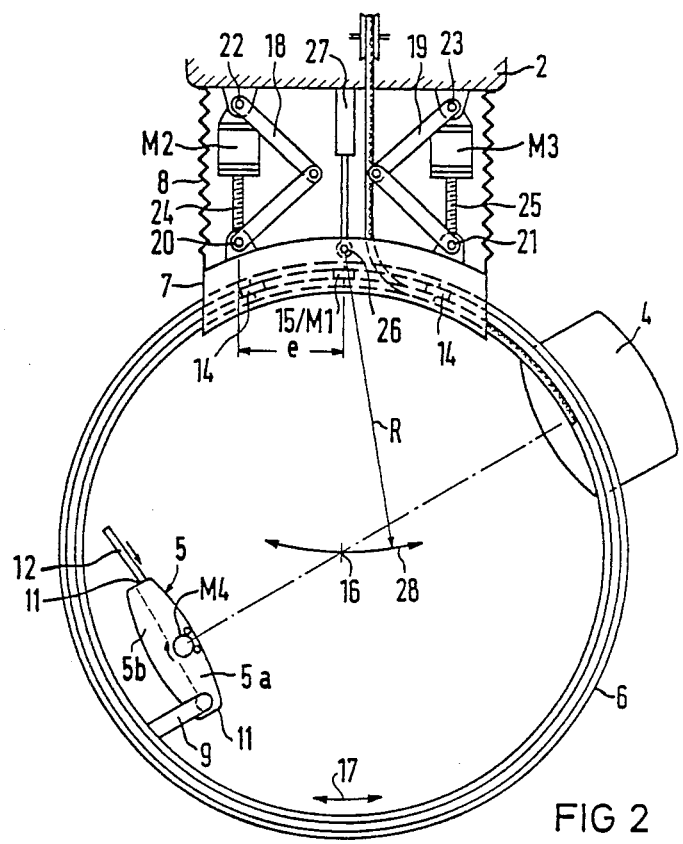
FIG. 2 is a plan view, partly in section, of a portion of the installation shown in FIG. 1.

As shown in FIG. 2, two scissor arms 18 and 19 are provided for adjusting the position of the ring 6. Respective first ends of the scissor arms 18 and 19 are hinged to the bearing 7 at points of articulation 20 and 21. The opposite second ends thereof are respectively hinged to the truck 2 at points of articulation 22 and 23. Electromotively driven spindle drives 24 and 25 are respectively disposed between the points of articulation 20 and 22 and the points of articulation 21 and 23. The spindle drives 24 and 25 are operated by drive units M2 and M3, which can be individually driven by a control unit described in greater detail below. A pivot bearing 26 is disposed at the bearing 7 centrally between the point of articulation 20 and 21 at a distance e. One end of a telescoping arm 27 is hinged to the pivot bearing 26, and the other end of the telescoping arm 27 is rigidly attached to the truck 2.

In combination with the scissors arm structure described above, the ring 6 and thus the position of the x-ray source 4 and the film cassette holder 5 can be brought to any desired rotational position around the head of the patient by appropriate control of the two drive units M2 and M3. If the drive units M2 and M3 are operated at the same speed, the ring 6 will be moved in a horizontal plane toward and away from the truck 2. If the drives M2 and M3 are non-uniformly adjusted, the ring 6 will be pivoted around off-center vertical axis 26 so that a center 16 of the ring 6 executes a transverse motion of about ±40 mm at a radius R of about 350 mm in the directions indicated by arrow 28 in a plane perpendicular to the vertical central axis 16.

In combination with the above-described pivotal motion, the ring 6 can also be rotated about its vertical central axis 16. It is accomplished by a drive unit M1 which includes a drive capstan 15 and guide rollers 14, all in contact with the ring 6. By simultaneously rotating and pivoting the ring 6, motion sequences can be achieved in a simple manner which, in conventional devices, require relatively complex linkages.

The drive capstan 15 and the guide rollers 14 are respectively disposed at the upper side and lower side of the ring 6 so as to form a triangular bearing. In a preferred embodiment, the drive capstan 15, coupled to the drive unit M1, is disposed at the upperside of the ring 6, and a guide roller 14 is disposed beneath the ring 6 at equal distances on opposite sides of the drive capstan 15. For this purpose, the bearing 7 may be formed in an appropriate angle.

Figure 5:
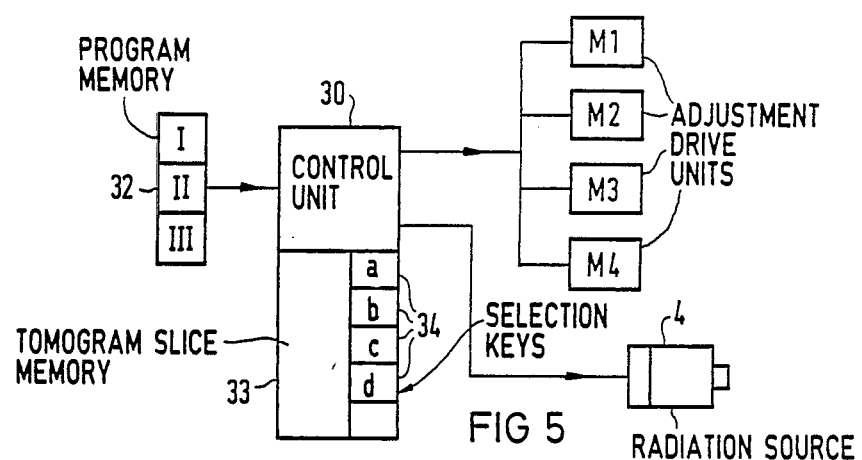
FIG. 5 is a block diagram schematically showing the various drive units and a control unit and memory therefore.

The film cassette holder 5 may consist of two half shells 5a and 5b joined at a longitudinal seam. The half shells 5a and 5b may be connected to each other by an easily releasibly screw connection, so that rapid access to the drive unit M4 is possible for service. Just as the drives M1, M2 and M3, the drive unit M4 for transporting the film cassette can be individually driven by the control unit 30 shown in FIG. 5.

Figure 3:
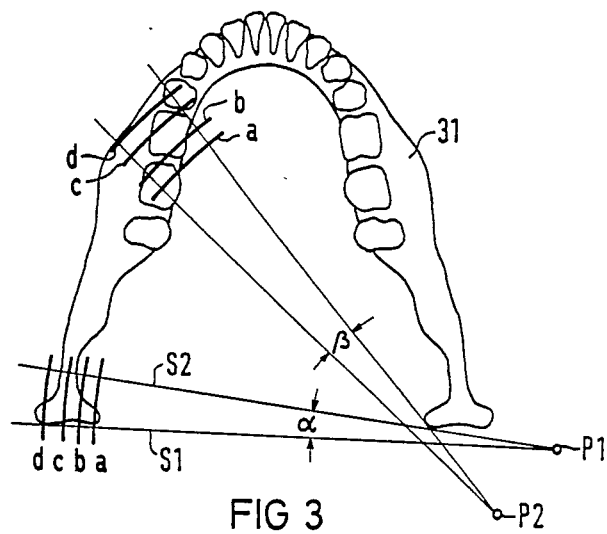
FIG. 3 is a plan view of a mandibular arch showing operation of the installation of the present invention.
Figure 4:
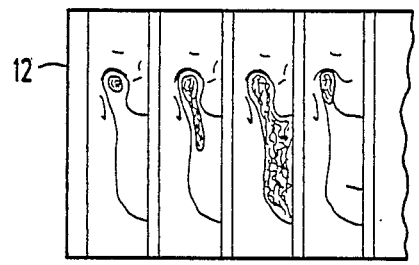
FIG. 4 is a simplified illustration of a developed x-ray film showing images in various tomogram positions.

The geometry for producing multi-slice exposures with the installation disclosed herein is shown in greater detail in FIGS. 3 and 4. FIG. 3 shows a schematic plane view of a mandibular arch 31. It is assumed that four different tomograms of the left temporomandibular point are to be produced first, and that four further tomograms of a different section of the jaw are to be subsequently produced.

By operation of the adjustment drive units M1, M2 and M3, the rotary unit 3 is brought to a position P1 from which the radiation source 4 can emanate rays to the desired imaging region which, for example, is within an angle $\alpha$ bounded by rays S1 and S2. The position P1 which the rotary unit 3 assumes is defined by values stored in a program memory 32 (see FIG. 5). The same is true of further positions P2 and the like for exposing further sections. Upon actuation of a program key I, corresponding signals are forwarded to the adjustment motors M1, M2 and M3 by the control unit 30, causing the rotary unit to move to the first initial position P1. The rotary unit is then caused to move to any number of further positions by actuating program keys II, III and so on.

The control unit 30 is connected to a further memory 33 in which corresponding memory values 33a through 33d are stored in accordance with the plurality of desired tomogram positions or slices, this number being four in the present exemplary embodiment. These memory values correspond to different speeds with which the drive motor M4 is operated and thus the speed with which the film cassette 12 will be moved through a secondary slit diaphragm in the film cassette holder 5. The desired tomogram slice is dependent on the speed with which the film cassette is conducted past the secondary diaphragm opposite a central ray from the source 4, thus different memory values corresponding to the desired tomogram slices can be stored in the memory 33. These memory values can be selected by tomograph position keys 34.

If, for example, proceeding from the initial position P1, an exposure of the left temporomandubular joint in accord with the pre-selected program I is desired in the tomogram slice a in FIG. 3, this tomogram position is pre-selected by the key 34a. The corresponding quantity communicated to the control unit 30 which operates the drive unit M4 past the central ray with a speed corresponding to the tomogram slice a. After exposure in the imaging section corresponding to the angel $\alpha$ has been completed for the slice a, the radiation source 4 is de-energized and the rotary unit is moved back by the swivel angle $\alpha$ to its initial position. Subsequently, the next exposure in a different tomogram slice (b, c or d) can be produced either individually by renewed actuation of another selection key 34 or automatically. The film cassette 12 is transported a greater distance during this repeated exposure, so that the subject details in the various tomogram positions are imaged next to one another on the film, as shown by schematic successive exposures Aa, Ab, Ac and Ad in FIG. 4.

Insofar as the length of the film in the cassette permits further subject excerpts to be imaged using an imaging excerpt to find by the angle $\alpha$, this procedure can be repeated proceeding from an arbitrary other location, for example, from the point P2. Again, proceeding from point P2, the selected subject excerpt is imaged in a plurality of slices (a through d) next to each other using, if necessary, a different angle such as β and the selected program. These different tomogram slices are also defined by different speeds of the drive unit M4 and are stored in the memory 33 and are called by one of the keys 34.

Although modifications and changes may be suggested by those skilled in the art it is the intention of the inventor to embody within the patent warranted hereon all changes and modifications as reasonably and properly come within the scope of his contribution to the art.

I claim as my invention:

1. An x-ray system for producing panorama tomograms of a plurality of selected slices at respectively different depths of the jaw and teeth of a patient comprising:
   support means including a truck;
   an x-ray source for making an x-ray exposure of said jaw and teeth;
   an x-ray film cassette;
   a carrier attached to and extending horizontally from said truck on which said x-ray source and a holder for said film cassette are disposed opposite each other with room for placement of said patient's jaw therebetween;
   first drive means in said holder for advancing said film cassette therein;
   second drive means for rotating said carrier around a central vertical axis such that the teeth and jaw of said patient are successively imaged on said film cassette;
   third drive means for pivoting said carrier in a plane perpendicular to said central vertical axis about an off-center vertical axis, said third drive means also being means for varying the distance between said central vertical axis and said off-center vertical axis, said first, second and third drive being separate; and
   control means for simultaneously controlling and coordinating operation of said x-ray source, said first drive means, said second drive means and said third drive means in combination, for constantly maintaining a perpendicular radiation transillumination direction relative to said film cassette through said patient and a substantially constant spacing between said patient and said film cassette while successively rotating said carrier during said exposure through a succession of selected equal angles corresponding to the same exposure area, but respectively different slices, of said patient to be imaged, for energizing said x-ray source during an exposure period and subsequently de-energizing said x-ray source to the beginning of a next angle in said succession, and for advancing said film cassette during an exposure at a speed during each exposure period for imaging one of said slices and for advancing said film cassette by a selected amount after each exposure.

2. An x-ray system as claimed in claim 1, further comprising a memory in said control unit for storing values corresponding to each of said plurality of selected slices.

3. An x-ray system as claimed in claim 2, further comprising means for manually selecting one of said slices for imaging.

4. An x-ray system as claimed in claim 1, further comprising a program memory connected to said control means for storing a plurality of programs respectively corresponding to a plurality of exposure excerpts, and means for manually selecting one of said exposure excerpts for imaging.

5. An x-ray system as claimed in claim 1, wherein said first drive means for advancing said film cassette is a stepping motor.

6. An x-ray system as claimed in claim 1, further comprising:
   means supporting said film cassette holder on said carrier for adjusting the position of said holder with respect to said x-ray source.

7. An x-ray system as claimed in claim 6, wherein said means for supporting said holder is an angled rod having one end rigidly attached to an interior of said carrier and an opposite end attached to said holder permitting rotation of said holder about said opposite end.

8. An x-ray system as claimed in claim 1, wherein said carrier is a ring and said means for rotating said carrier includes a drive motor connected to said control means, a drive capstan connected to said drive motor disposed on one side of said ring, and at least one guide roller disposed on an opposite side of said ring.

9. An x-ray system as claimed in claim 8, wherein said means for rotating said ring includes two guide rollers respectively disposed equidistantly oppositely laterally of said drive capstan.

10. An x-ray system as claimed in claim 1, wherein said carrier is a ring and said means for pivoting includes a rod connected between said truck and said ring and two independently operable drive linkages respectively disposed on opposite sides of said rod between said truck and said ring.

11. An x-ray system as claimed in claim 10, wherein each of said drive linkages comprises:
    a motor;
    a threaded drive shaft rotated by said motor; and
    a scissors arm having opposite free ends with a hinged joint therebetween, said opposite free ends of said scissors arm being respectively connected to said truck and to said ring with said motor and said shaft therebetween.

12. An x-ray system as claimed in claim 10, wherein said rod is a telescoping rod.

13. An x-ray system for producing panorama tomograms of a plurality of slices at respectively different depths of the jaw and teeth of a pataient comprising:
    a support assembly;
    an x-ray source for making an x-ray exposure of said jaw and teeth;
    an x-ray detector having film and first drive means for advancing said film at a plurality of speeds, each speed corresponding to one of said tomograms of one of said slices, said x-ray detector being disposed a horizontal distance from said x-ray source aligned with a central ray emanating from said x-ray source;
    second drive means for rotating said x-ray source and said x-ray detector in a circle centered on a first point within said central ray;
    third drive means for pivoting said first point centered within said central ray through an arc centered about a second point spaced from said first point and for varying the distance between said first point and said second point;

means for attaching said second drive means and said third drive means to said support assembly; and control means for simultaneously controlling and coordinating operation of said first drive means, said second drive means and said first drive means, said second drive means and said third drive means in combination, for constantly maintaining a perpendicular radiation transillumination direction relative to said x-ray detector through said patient and a substantially constant spacing between said x-ray source and said x-ray detector through a succession of selected equal angles during an exposure period corresponding to the same exposure area, but respectively different slices, of said patient to be imaged, and for advancing said film during said exposure period at a speed such that one os said slices in imaged.

14. An x-ray system as claimed in claim 13, wherein said second drive means includes a ring carrier on which said x-ray source and said x-ray detector are mounted opposite each other.

15. An x-ray system as claimed in claim 14, wherein said third drive means includes a rod connected between said support assembly and said ring and independently operable drive linkages disposed on opposite sides of said rod between said ring and said support assembly.

16. An x-ray system as claimed in claim 15, wherein said rod is compressible and expandible.

17. An x-ray system as claimed in claim 16, wherein said rod is a telescoping rod.

* * * * *